US012778707B2

(12) United States Patent
Hahn

(10) Patent No.: US 12,778,707 B2
(45) Date of Patent: Nov. 3, 2026

(54) MEDICAL QUICK COUPLING SYSTEM FOR ATTACHING A GUIDE SLEEVE WITHOUT TOOLS

(71) Applicant: B. Braun New Ventures GmbH, Freiburg (DE)

(72) Inventor: Lukas Hahn, Sigmaringen (DE)

(73) Assignee: B. Braun New Ventures GmbH, Freiburg (DE)

( * ) Notice: Subject to any disclaimer, the term of this patent is extended or adjusted under 35 U.S.C. 154(b) by 143 days.

(21) Appl. No.: 18/795,472

(22) Filed: Aug. 6, 2024

(65) Prior Publication Data

US 2025/0049531 A1 Feb. 13, 2025

(30) Foreign Application Priority Data

Aug. 9, 2023 (DE) ..................... 10 2023 121 252.4

(51) Int. Cl.
*A61B 90/11* (2016.01)
*A61B 17/00* (2006.01)
*A61B 34/30* (2016.01)

(52) U.S. Cl.
CPC ............. *A61B 90/11* (2016.02); *A61B 17/00* (2013.01); *A61B 2017/00486* (2013.01); *A61B 34/30* (2016.02)

(58) Field of Classification Search
CPC .. A61B 2017/2215; A61B 2017/00477; A61B 2018/00172; A61B 2017/0046; A61B 2017/00464; A61B 2017/00469; A61B 2017/00486; A61B 17/162; A61B 17/17–1796; A61B 2017/00482; A61B 2017/00473; A61B 17/02–0293; A61B 2017/347; A61B 17/3462; Y10T 279/17102; Y10T 279/17094; Y10T 279/17145; Y10T 279/17752; Y10T 279/17196; B23B 31/1071
See application file for complete search history.

(56) References Cited

U.S. PATENT DOCUMENTS 6,099,537 A * 8/2000 Sugai ................ A61B 17/1285 606/205
2002/0095177 A1* 7/2002 Kupferschmid ....... A61B 17/29 606/1

* cited by examiner

*Primary Examiner* — Thomas McEvoy
(74) *Attorney, Agent, or Firm* — Christopher A. Rothe; CM Law

(57) ABSTRACT

A medical quick coupling system includes a guide sleeve into which a medical instrument or medical device can be received and aligned or oriented. A quick coupling includes a radially inner carrier sleeve, in which the guide sleeve can be received and aligned or oriented, and a radially outer actuating sleeve that is movable relative to the carrier sleeve, with a receiving position and a fixing position. A coupling mechanism is arranged between the actuating sleeve and carrier sleeve, so that insertion of the guide sleeve into the quick coupling moves the coupling mechanism from a disengaged position to an engaged position. The coupling mechanism thereby disengages the actuating sleeve from the receiving position into the fixing position. Actuation of the actuating sleeve from the fixing position against a pretension force into the receiving position moves the coupling mechanism from the engaged position into the disengaged position.

11 Claims, 6 Drawing Sheets

MEDICAL QUICK COUPLING SYSTEM FOR ATTACHING A GUIDE SLEEVE WITHOUT TOOLS

CROSS-REFERENCE TO RELATED APPLICATION

This application claims priority under 35 U.S.C. § 119 to German Application No. 10 2023 121 252.4, filed on Aug. 9, 2023, the content of which is incorporated by reference herein in its entirety.

FIELD

The present disclosure relates to a medical quick coupling system for the tool-free mounting of a guide sleeve.

BACKGROUND

A basic requirement for machine-assisted, medical or surgical interventions is the precise guidance of a medical instrument or device. The medical instrument or device is, for example, connected to a robot-guided surgery system or to an arm alignment system. Instruments or devices guided in this way are used, for example, in frameless stereotactic surgery or spinal surgery. The precise connection and alignment of the instrument or device is carried out via a respective guide sleeve, which has at least one axial direction or orientation.

Current solutions connect the guide sleeves using a screw solution. The guide sleeve is fixed to the interface with a lateral screw. This has the disadvantage that connecting the guide sleeve takes a lot of time and it is difficult to align the height and direction of the guide precisely. The use of a lateral fixing screw also does not provide centric clamping of the guide sleeve and can therefore influence the preciseness and angle of the working axis. In addition, the user must screw and unscrew the fixing screw to secure and loosen the guide sleeve, which requires two user interactions. There is no reliable feedback as to whether the guide sleeve is connected at the correct height and orientation.

Other alignment systems for guide sleeves have a fixed diameter for the guide sleeve. Here, however, the application is limited to instruments with only one diameter. Alternatively, a set of different instruments with guide sleeves integrated directly on the instruments must be provided. This leads to a limited use of instruments or to a high financial expenditure, since a set of instruments must be developed for each indication.

SUMMARY

Therefore, it is the task of the present disclosure to avoid or at least reduce the disadvantages of the prior art and in particular to provide a medical quick coupling system for the tool-free receptacle of guide sleeves, with which a plurality of medical, in particular surgical, instruments or devices can be connected by means of the received guide sleeve in a simple manner for the operator and with repeatable accuracy. A subtask can be seen in simply picking up and coupling of a set of different guide sleeves, which are adapted for special instruments or devices, as well as quickly and easily changing of these intra-operatively as needed.

The task of the present disclosure is solved with respect to the medical quick coupling system according to the present disclosure.

A basic notion of the present disclosure provides for a medical, in particular surgical, quick coupling system for guide sleeves having different inner diameters, by means of which different medical instruments or devices, having different diameters, can be easily, quickly and repeatedly connected to a robot-guided surgery system or to a mechanical arm alignment system.

In a specific embodiment, a medical, in particular surgical, quick coupling system is provided and designed for tool-free coupling or connection or reception of a guide sleeve. For this purpose, the quick coupling system has at least one, in particular separate, guide sleeve and a quick coupling. The guide sleeve has a guide axis, in particular a longitudinal axis. A medical instrument or a medical device can be accommodated in the guide sleeve and aligned or oriented in the direction of the guide axis. The quick coupling has a, in particular coaxially arranged, in particular radially inner carrier sleeve or carrier structure, in which the guide sleeve can be received and aligned or oriented. A radially outer actuating sleeve, which is in particular arranged coaxially is provided so as to be movable relative to the carrier sleeve and has a first receiving position and a second fixing position. It assumes the first receiving position in particular when the guide sleeve is disengaged, and it assumes the second fixing position in particular when the guide sleeve is engaged. Furthermore, the quick coupling has a coupling mechanism arranged between the actuating sleeve and the carrier sleeve, which is adapted so that an insertion or pressing of the guide sleeve into the quick coupling, in particular into the carrier sleeve, moves the coupling mechanism from a first disengaged position, in which in particular the guide sleeve is disengaged, to a second engaged position, in which in particular the guide sleeve is engaged, wherein the coupling mechanism moves thereby moves the actuating sleeve from the receiving position to the fixing position. The coupling mechanism is further adapted so that engaging the actuating sleeve from the fixing position against a pretensioning force into the receiving position, moves the coupling mechanism from the second, engaged position to the first, disengaged position and thus releases the guide sleeve.

In this way, a medical quick-release coupling system is realized, in which the user moves the guide sleeve into its intended orientation by simply inserting or pressing the guide sleeve into the quick-release coupling-without the need for a mounting tool. The first receiving position of the actuating sleeve, which indicates the disengaged guide sleeve, and the second fixing position of the actuating sleeve, which indicates the engaged guide sleeve, provide clear haptic and optical feedback on the coupling state of the guide sleeve, whether it is correctly received and oriented, or not.

Medical instruments or devices are in particular a surgical drill, a biopsy needle, an endoscope, surgical standard instruments, an electrode and the like.

According to a preferred further advancement, the quick-release coupling system comprises a plurality of separate guide sleeves, the interfaces of which are the same or at least have the same effect to the coupling mechanism, whereas their receptacles are different for receiving the respective instrument or device. In other words: A variety of medical instruments or devices can be connected using the same quick coupling. For this purpose, only the respective guide sleeve must be selected and pressed into the quick coupling. To change, the actuating sleeve must be moved from the second fixing position back into the first receiving position, and the coupling mechanism releases the current guide sleeve or ejects it at least in sections.

According to a preferred further advancement, the coupling mechanism has at least one actuating element, in particular one actuating pin, preferably at least two diametrically or more than two, actuating elements arranged evenly distributed, wherein the at least one actuating element is formed by a preferably elongated hole-shaped, through-way recess of the carrier sleeve or carrier structure projecting radially into a coupling or attachment or receiving space of the carrier sleeve, so that the at least one actuating element can be taken from the guide sleeve during insertion or pressing in the insertion direction. In this way, the coupling mechanism can be actuated directly by inserting or pressing it into the guide sleeve and actuating the coupling mechanism by separate means. Therefore, the medical quick coupling system does not require any special tools for inserting or pressing it into the guide sleeve and proves to be extremely user-friendly.

According to a preferred further advancement, the guide sleeve has at least one actuating section, which is provided and designed to engage with the at least one actuating element during insertion or pressing. The system is preferably designed in a form-locking manner at least in axial direction or insertion direction.

According to a preferred further advancement, the guide sleeve has an alignment structure, in particular a geometric one, and the quick coupling has a complementary counterstructure, which interact with each other in order to realize a rotationally fixed reception of the guide sleeve and subsequently enable a rotational orientation of the medical instrument or device guided in the guide sleeve.

According to another, preferred further advancement, the at least one actuating section of the guide sleeve is formed by a radially extending end face or end surface of a guide groove or guide recess extending in the insertion direction at a distal end section. In other words: the at least one actuating section of the guide sleeve is preferably formed on an end section of a guide groove or guide recess, in particular on an end face or end surface of the guide groove or guide recess.

According to another, preferred further advancement, a plurality of guide grooves or guide recesses comprising the end faces or end surfaces are arranged circumferentially distributed on the guide sleeve. Preferably, they are evenly distributed around the circumference so that they can specify a rotation angle division of the guide sleeve in the quick coupling.

An insertion section of the guide sleeve, into which the guide grooves or guide recesses ends are chamfered or rounded according to another preferred advancement. These tapered ends form an insertion aid of the at least one actuating element into the respective guide groove or guide recess, or a sliding aid of the respective guide groove or guide recess onto the at least one actuating element.

According to another, preferred further advancement, the coupling mechanism has two coaxially arranged first and second coupling sleeves in an intermediate space between the carrier sleeve and the actuating sleeve and axially displaceable with respect to each other.

Viewed in axial direction, the first radially inner or inner coupling sleeve preferably has a first sleeve section having a larger, first inner diameter and a second sleeve section having a smaller, second inner diameter.

The first, radially inner coupling sleeve in particular interacts with a first, radially inner locking means of the coupling mechanism, in that the first, radially inner coupling sleeve by moving over the first, radially inner locking means of the larger, the first inner diameter to the smaller, second inner diameter of the first, radially inner coupling sleeve, engages or presses the first, radially inner locking means radially inward and in particular fixes it, wherein the first radially inner latching means engages in the guide sleeve in a form-locking manner, so that the guide sleeve is coupled to the carrier sleeve. Conversely, the first radially inner coupling sleeve interacts with the first radially inner locking means of the coupling mechanism in such a way that the first radially inner coupling sleeve releases the first radially inner locking means radially outward again when moving back from the smaller, second inner diameter to the larger, first inner diameter, so that the guide sleeve is disengaged from the carrier sleeve.

According to another, preferred further advancement, the second, radially outer or external coupling sleeve also has a first sleeve section with a larger, first inner diameter and a second sleeve section with a smaller, second inner diameter when viewed in the axial direction.

The second, radially outer coupling sleeve preferably interacts with a second, radially outer locking means of the coupling mechanism in such a way that the second, radially outer coupling sleeve by moving over the second, radially outer locking means of the larger, the first inner diameter to the smaller, second inner diameter of the second, radial outer coupling sleeve, engages or presses the second, radially outer locking means radially inward and in particular fixes it, wherein the second, radially outer locking means engages in a form-locking manner in the carrier sleeve, so that the first, radially inner coupling sleeve is fixed to the carrier sleeve. Conversely, the second, radially outer coupling sleeve interacts with the second, radially outer locking means of the coupling mechanism in such a way that the second, radially outer coupling sleeve releases the second, radially inner locking means radially outward when the smaller, second inner diameter is moved back to the larger, first, radially outer coupling sleeve, so that the first, radially inner coupling sleeve is no longer fixed to the carrier sleeve.

The first, radially inner locking means is preferably formed by first balls, which are received in a radially movable manner in a circumferentially distributed radial through-recesses of the carrier sleeve. The first balls preferably have a first ball diameter that exceeds a wall thickness of the carrier sleeve in the area of the first radial through-recesses. As a result, the first balls can project radially inward into the receiving space of the carrier sleeve while simultaneously be in radial outward contact with the smaller, second inner diameter of the first, radially inner coupling sleeve. Therefore, the first, radially inner coupling sleeve can engage the first balls in a coupling recess of the guide sleeve adapted to the first balls and thus couple and fixate the guide sleeve on the carrier sleeve.

An inner diameter of the first radial through-recesses is tapered toward the carrier sleeve preferentially toward an inner diameter that is smaller than the first ball diameter. In this way, the first balls can—as described—be pressed radially inwards, as described, but are secured against falling out into the receiving space.

The second, radially outer locking means is preferably formed by second balls, which are received in a radially movable manner in a circumferentially distributed radial through-recess of the carrier sleeve. The second balls preferably have a second ball diameter that exceeds a wall thickness of the first radially inner coupling sleeve in the area of the second radial through-recesses. This allows the second balls to engage in a coupling recess in the carrier sleeve adapted to the second balls and at the same time to be in radial contact with the smaller, second inner diameter of the second, radially outer coupling sleeve. Therefore, the second, radially outer coupling sleeve can define the first, radially inner coupling sleeve on the carrier sleeve by means of the second balls.

On a first front end portion of the first, radially inner coupling sleeve, a first circular cylindrical recess having the first, larger inner diameter is formed, in particular radially on the inside, to which a radial shoulder, preferably inclined or conical, adjoins in the direction of a second front end portion of the first, radially inner coupling sleeve. The radial shoulder is preferably tapered in the direction toward the second front end section of the first, radially inner coupling sleeve down to the smaller, second inner diameter. The thus tapered radial shoulder is followed by a second circular cylindrical recess which extends with the second, smaller inner diameter up to the second front end section of the first, radially inner coupling sleeve.

The second through-recesses are preferably formed in the area of the second, smaller inner diameter of the first, radially inner coupling sleeve, and a respective of the second balls is arranged in the second through-recesses.

On the second front end section of the first radially inner coupling sleeve, a flange or a shoulder, preferably extends around the outside circumference, in particular separated into partially circumferential flange portions, preferably into two diametrically arranged flange portions. The flange or shoulder receives at least two connecting pins from the radial outside, via which the first, radially inner coupling sleeve is motion-coupled to the actuating sleeve, in particular firmly connected.

Preferably, the flange or the shoulder of the first, radially inner coupling sleeve forms a stop or a support for the second spring.

On a first front end portion of the second, radially outer coupling sleeve, a first circular cylindrical recess having the first, larger inner diameter is formed, in particular radially on the inside, to which a preferably conical radial shoulder adjoins in the direction of a second front end portion of the second, radially outer coupling sleeve. This radial shoulder tapers in the direction towards the second end section of the second radially outer coupling sleeve to the smaller, second inner diameter of the second radially outer coupling sleeve. The thus tapered radial shoulder is followed by a second circular cylindrical recess which extends with the second, smaller inner diameter up to the second front end section of the second, radially outer coupling sleeve.

The second, radially outer coupling sleeve is preferably longer in the axial direction of movement than the first, radially inner coupling sleeve.

The second, front end section of the second, radially outer coupling sleeve is preferably divided in the area of the second, smaller inner diameter into, preferably two, partially circumferential sleeve sections.

The partially circumferential sleeve sections are preferably aligned with respect to their circumferential elongation to the partially circumferential flange sections of the first, radially inner coupling sleeve, and engage in flange gaps extending partially circumferentially between the flange sections, so that an axial and torsion-proof guide of the second, radially outer coupling sleeve is realized on the first, radially inner coupling sleeve, and vice versa.

In particular on the first front end section of the second, radially outer coupling sleeve, a flange or a shoulder extends around the outside circumference, preferably over the entire circumference, from which a stop or a support of the second spring is formed.

Preferably, the second spring is designed as an annular spring or spiral spring and surrounds the second radially outer coupling sleeve on the outside.

On the partially circumferential sleeve sections of the second, radially outer coupling sleeve, preferably close to the front side of the second end section, at least one through-bore, preferably one through-bore per sleeve section, is provided, to which the respective actuating element is fastened, preferably pressed in and projects radially inward.

The carrier sleeve preferably has one elongated hole per actuating element, through which the respective actuating element extends into the receiving space of the carrier sleeve. Through this or these elongated holes, the second, radially outer coupling sleeve, which is coupled in motion to the actuating element(s), is limited in its axial stroke and is also secured against rotation relative to the carrier sleeve.

The carrier sleeve has preferentially one elongated hole per connecting pin. The connecting pins preferably engage through the flange of the first, radially inner coupling sleeve from the radial outside to a receiving space arranged radially inward of the first, radially inner coupling sleeve, in which the carrier sleeve is received. End sections of the connecting pins engage in the respective associated elongated hole of the carrier sleeve. In this way, the respective connecting pin can only execute a limited axial stroke, so that the first radially inner coupling sleeve coupled to the connecting pins and the actuating sleeve are limited in their axial stroke and are secured against rotation with respect to the carrier sleeve. The actuating sleeve can thus execute an axial stroke only between its first receiving position and its second fixing position.

The coupling recess of the guide sleeve, which is adapted to the first balls, is in a first variant a spherical recess per first ball and in a second variant a circumferential groove. In the first variant, the guide sleeve can only be orientated in one or more defined rotational positions in the quick coupling. In the second variant, the guide sleeve can be orientated in any rotational position in the quick coupling.

According to another, preferred further advancement, the first radially inner coupling sleeve is coupled to the actuating sleeve in a motion-coupled manner, in particular by means of a pin connection or due to a one-piece configuration. In this way, the position of the actuating sleeve always clearly and visibly indicates the position of the coupling mechanism with respect to the engagement and the disengagement of the guide sleeve.

According to another, preferred further advancement, the second, radially outer coupling sleeve is coupled with the at least one actuating element in a motion-coupled manner, in particular by means of a press-in connection or due to a one-piece configuration. In this way, the guide sleeve can directly actuate the second, radially outer coupling sleeve during insertion or pressing, and conversely, the second, radially outer coupling sleeve can eject the guide sleeve directly from the carrier sleeve, at least in section, when disengaging.

In order to apply the aforementioned pretensioning force, the coupling mechanism according to a further advancement comprises a first spring, preferably a compression spring, through which the actuating sleeve is loaded in the direction of the second fixing position and the first, radially inner coupling coupled to the actuating sleeve in the direction of overrunning the first radially inner locking means by the larger, first inner diameter to the smaller, second inner diameter.

In order to pretension in particular the first coupling sleeve against the second coupling sleeve, the coupling mechanism according to a further advancement comprises a second spring, which is preferably connected in series to the first spring, and which is preferably a pressure spring, through the second radially outer coupling sleeve on the first, radially inner coupling sleeve is supported, and from the second, radially outer coupling sleeve in the direction of the travel over the second, radially outer locking means of the larger, the first inner diameter to the smaller, second inner diameter.

The quick coupling system can, in particular, comprise a set of guide sleeves having at least a first guide sleeve and a second guide sleeve, wherein a geometric design of the first guide sleeve differs from the second guide sleeve by a different receptacle, such as an inner contour, in order to provide a suitable guide sleeve for different instruments or devices. In other words, the interfaces of the guide sleeves that act on the coupling mechanism are the same or at least have the same effect, whereas their receptacles for holding the respective instrument or device are designed differently.

BRIEF DESCRIPTION OF THE DRAWINGS

The present disclosure is explained below in more detail with reference to preferred embodiments with reference to the accompanying figures.

The figures are schematic in nature and are only intended to aid understanding of the present disclosure. The features of the various embodiments can be interchanged.

DETAILED DESCRIPTION

According to the disclosure, the following describes how a medical quick coupling system is constructed and how it engages and disengages a guide sleeve of a medical instrument so that the rapid and repeatable exchange and the correspondingly safe orientation of a medical instrument or device on a robot-guided surgical system or on an arm alignment system can be carried out.

Figure 1:
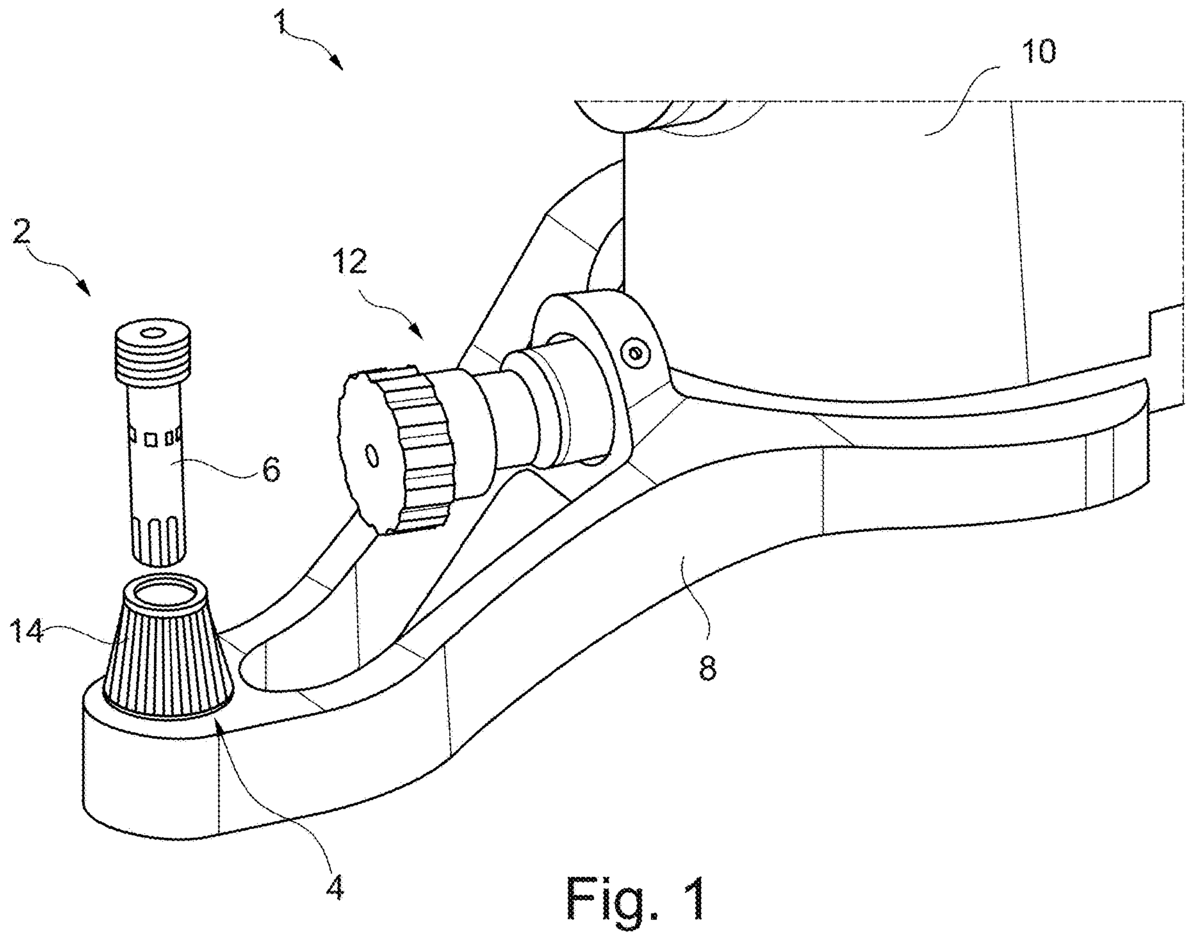
FIG. 1 shows a perspective view of a medical quick coupling system with a quick coupling and guide sleeve according to an exemplary embodiment, arranged on an adapter of a robotic end segment.

FIG. 1 shows in a perspective view of a medical quick coupling system 2 with a quick coupling 4 with a radially outer concave, conical actuating sleeve 14 and a receiving and coupling guide sleeve 6, which can be inserted into the quick-release 4 according to an exemplary embodiment. The quick coupling 4 is fixedly arranged on a fork-shaped medical fastening adapter 8, which in turn is fastened to an end segment 10 of a surgical robot. The fastening of the fastening adapter 8 can be detached at the end segment 10 and this is accomplished in the shown exemplary embodiment by means of a three-point support of a three-part coupling structure (not shown). A fastening position of the fastening adapter 8 on the end segment 10 can be varied between at least two layers by means of an adjusting means 12 designed as a screw gear.

FIGS. 2 to 5 show the quick coupling system 2 with the actuating sleeve 14 and the guide sleeve 6 according to FIG. 1 in a side view, or rather in a perspective side view.

Figure 2:
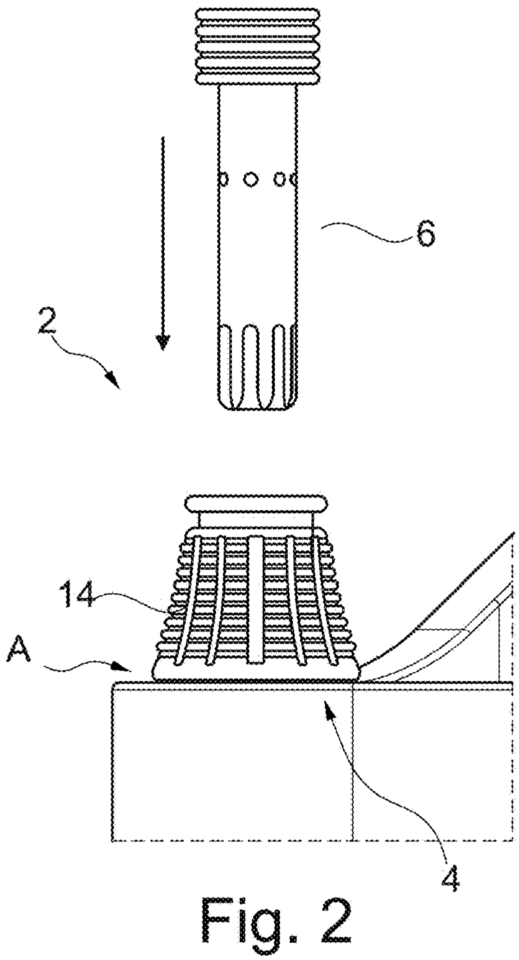
FIG. 2 shows a side view of the medical quick coupling system according to FIG. 1 with a first receiving position and with the guide sleeve disengaged.

FIG. 2 shows the actuating sleeve 14 in its first receiving position A, in which it is maximally distally arranged and fixed in an insertion direction of the guide sleeve, and in which the guide sleeve 6 is not yet inserted into the quick coupling 4 and is therefore still disengaged.

Figure 3:
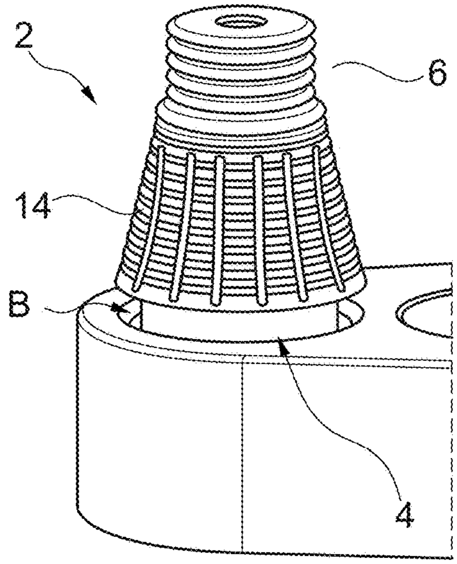
FIG. 3 shows a perspective side view of the medical quick coupling system according to FIGS. 1 and 2 with a second fixing position and with an engaged guide sleeve.

FIG. 3 shows the actuating sleeve 14 in its second fixing position B, in which it is arranged at most proximally in an insertion direction of the guide sleeve and in which it is prestressed by means of a pretensioning force of a first spring (not shown). The guide sleeve 6 is inserted into the quick coupling 4 and coupled.

Figure 4:
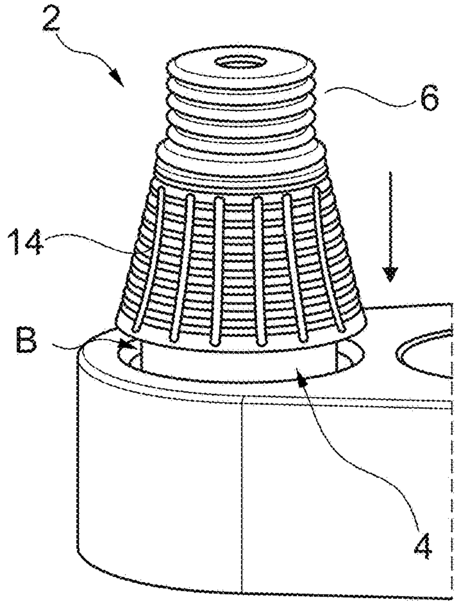
FIG. 4 shows a perspective side view of the medical quick coupling system according to FIG. 3 with illustrated actuating direction for disengaging the coupled guide sleeve.

FIG. 4 shows, like FIG. 3, the actuating sleeve 14 in its second fixing position B. In addition, it shows an actuating direction of the actuating sleeve 14 (arrow downwards) with which the disengagement of the coupled guide sleeve 6 is triggered.

Figure 5:
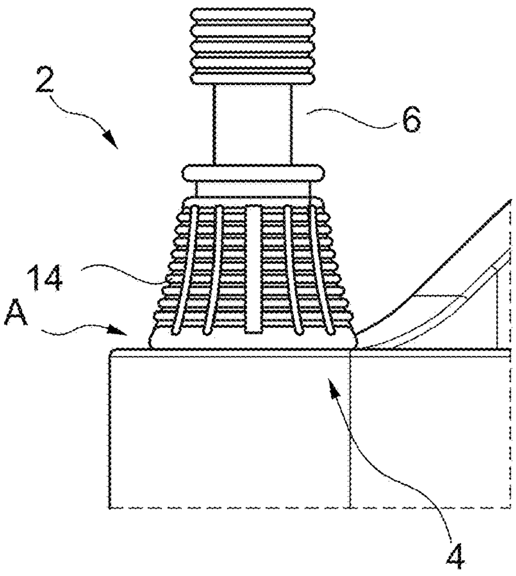
FIG. 5 shows a side view of the medical quick coupling system according to FIGS. 1 through 4 with the first receiving position and with the guide sleeve disengaged and partially ejected.

Finally, FIG. 5 shows the medical quick coupling system 2 according to FIGS. 1 through 4 following the actuation of the actuating sleeve 14 in its actuation direction according to FIG. 3 and in its first receiving position A, which it resumed after said actuation. A coupling mechanism (see the following figures) of the quick coupling 4 has partially ejected the disengaged guide sleeve 6, so that it can be easily gripped for a change.

Figure 6:
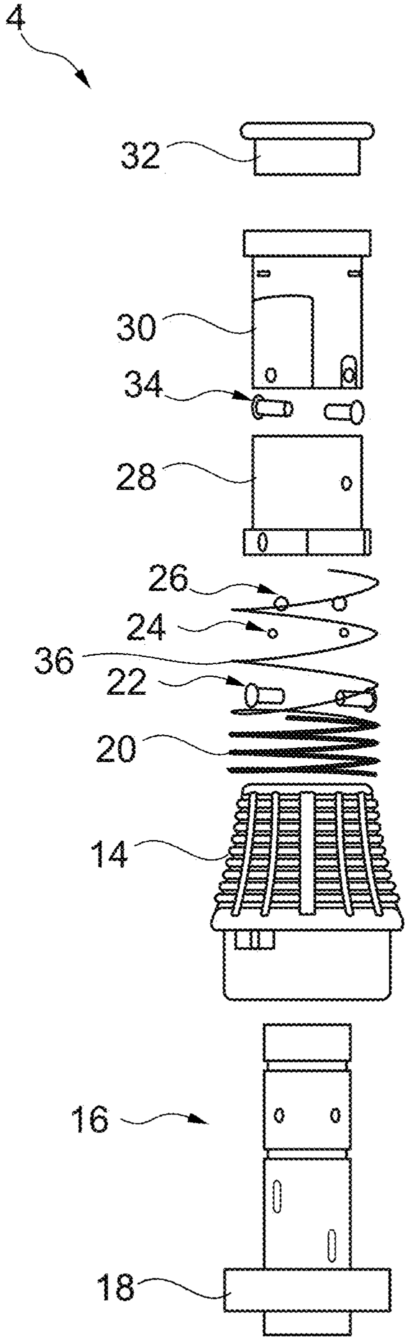
FIG. 6 shows an exploded view from the side of the quick coupling of the medical quick coupling system according to FIGS. 1 through 5.

FIG. 6 shows an exploded view from the side of the quick coupling 4 of the medical quick coupling system 2 according to FIGS. 1 through 5. Along the insertion or longitudinal axis of the quick coupling system 2, the following are arranged from bottom to top, or from distal to proximal: a carrier sleeve 16 with a fastening flange 18 at the distal end, the actuating sleeve 14, a first spring 20, two diametrically arranged connecting pins 22, a second spring 36, two diametrically arranged second balls 24, two diametrically arranged first balls 26, a first, radially inner coupling sleeve 28, actuating elements 34, a second, radially outer coupling sleeve 30 and a stop sleeve 32 arranged at the proximal end.

Figure 7:
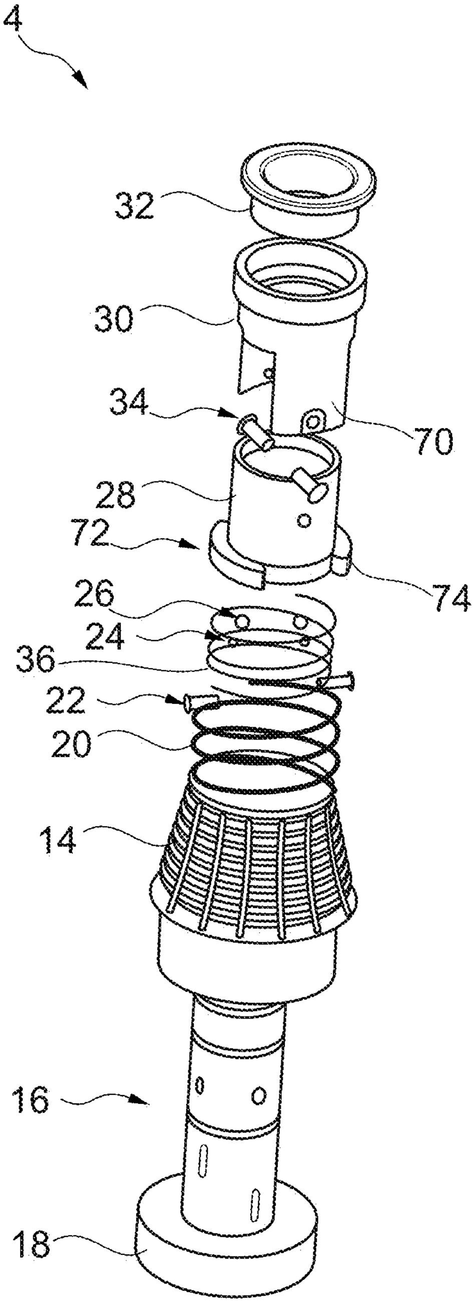
FIG. 7 shows a perspective exploded view of the quick coupling according to FIG. 6.

FIG. 7 shows the exploded view of the quick coupling 4 of the medical quick coupling system 2 according to FIG. 6 in a perspective view from the side.

Figure 9:
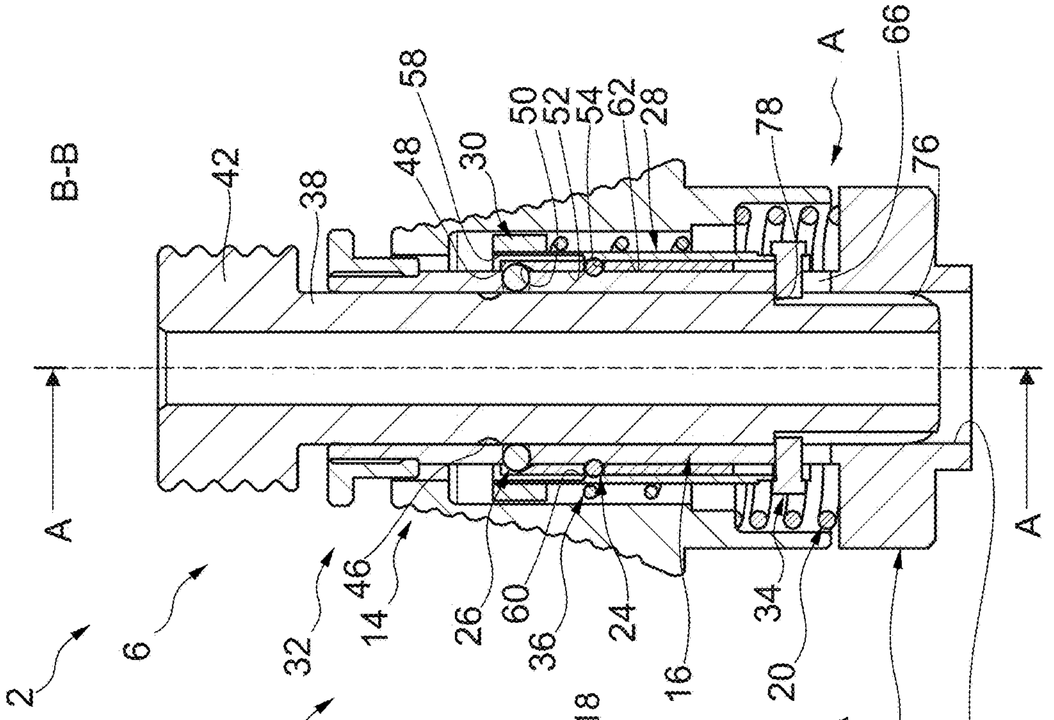
FIG. 9 shows a longitudinal section of the medical quick coupling system according to FIG. 8 guided through the guide axis and offset by 90 degrees to the longitudinal section according to FIG. 8.
Figure 8:
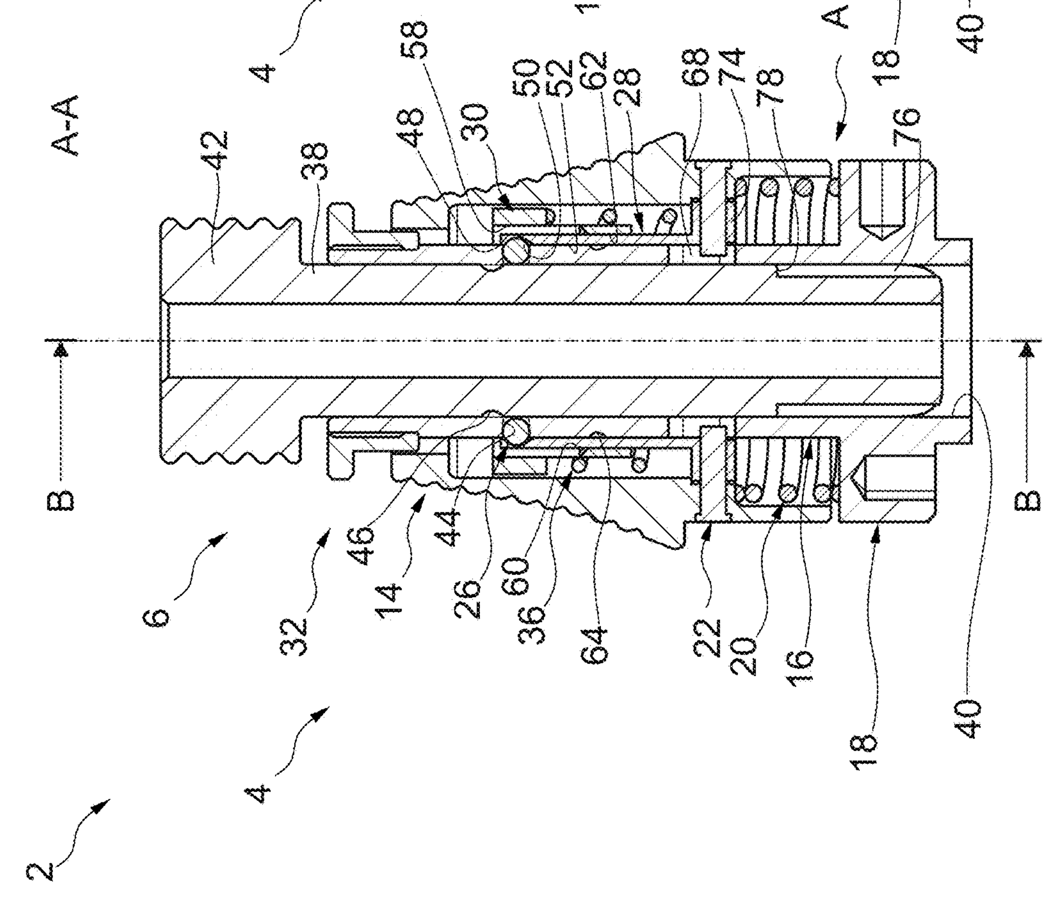
FIG. 8 shows a longitudinal section of the medical quick coupling system guided by a guide axis according to FIGS. 1 through 7.
Figure 11:
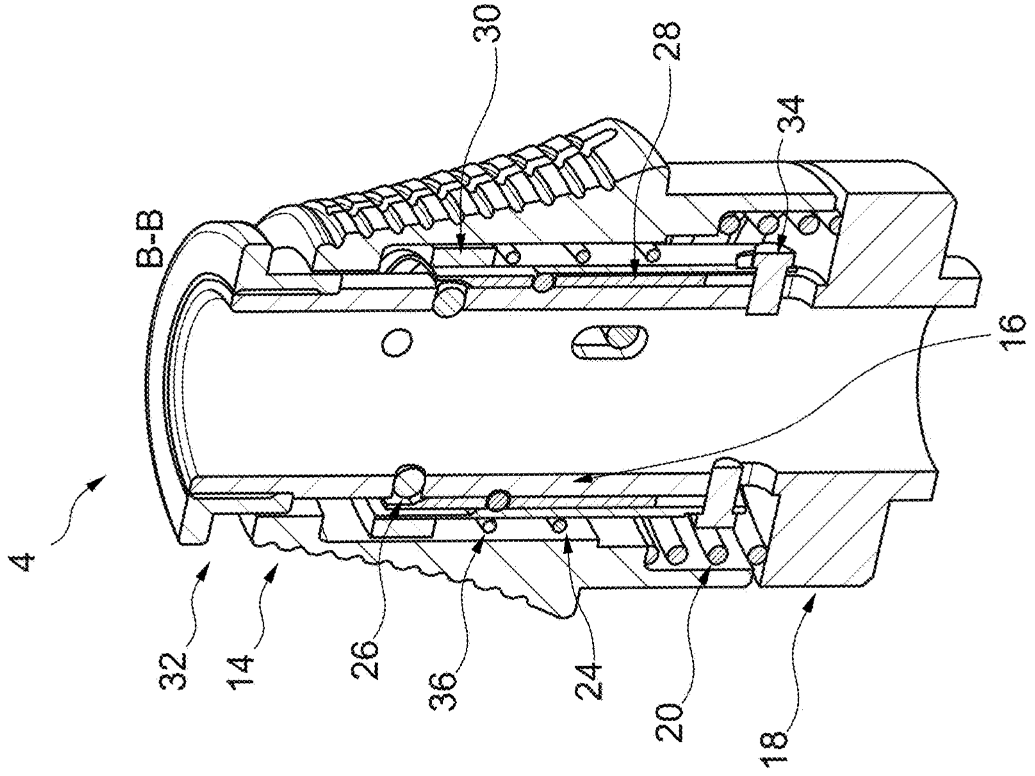
FIG. 11 shows the longitudinal section according to FIG. 9 in a perspective view.
Figure 10:
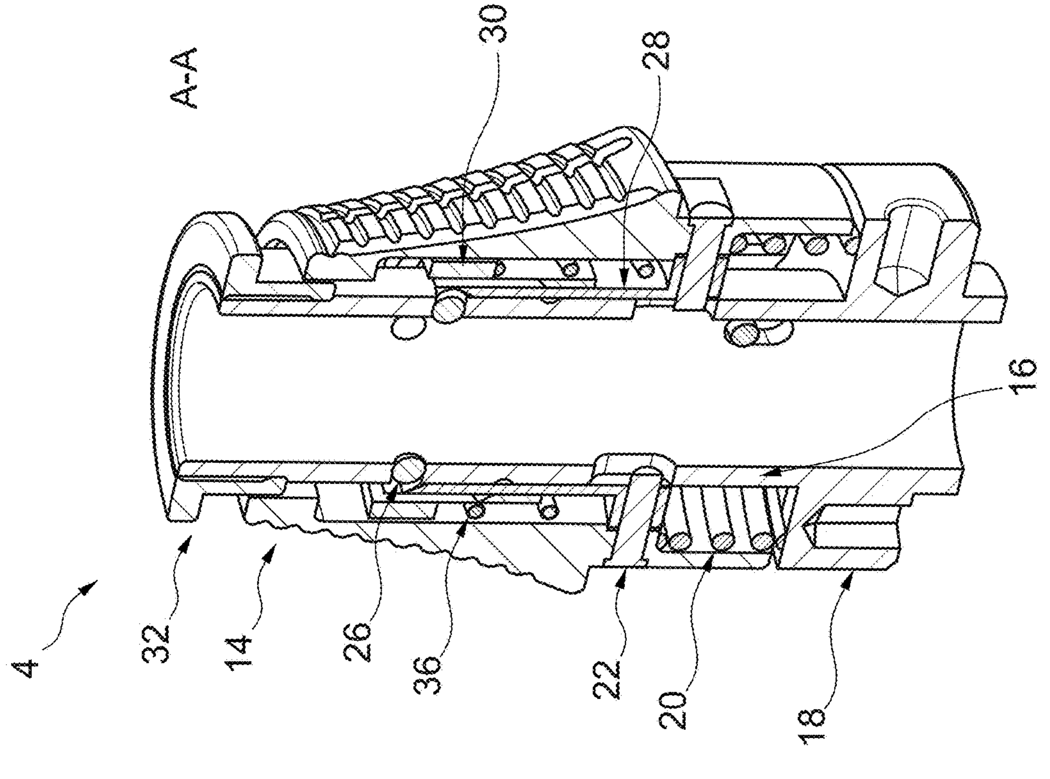
FIG. 10 shows the longitudinal section according to FIG. 8 in a perspective view.

FIG. 8 shows a longitudinal section of the medical quick coupling system 2 according to FIGS. 1 through 7 guided through a guide axis of the guide sleeve 4; FIG. 9 shows a longitudinal section of the medical quick coupling system 2 rotated by 90 degrees in relation to the longitudinal section according to FIG. 8; FIG. 10 shows a perspective view of the longitudinal section of the quick coupling according to FIG. 8 (without guide sleeve) and FIG. 11 shows a perspective view of the longitudinal section according to FIG. 9 (also without guide sleeve).

With reference in particular to FIGS. 8 through 11, the structural design and the mode of action of the quick coupling system 2 are described.

According to FIG. 8, the guide sleeve 6 with a guide shaft 38 is inserted into a cylindrical receiving space 40 of the carrier sleeve 16 of the quick coupling 4 and it is in a disengaged state. On a proximal end section, the guide sleeve 6 comprises a radially expanded, externally grooved head section 42, which, due to its knurling, is suitable for manual gripping or, for example, for coupling a device for adjusting the height of an instrument or device on the guide sleeve 6.

Contrary to the pretensioning force of the first spring 20, the actuating sleeve 14 of the quick coupling 4 is offset into its first receiving position A and is thus located near the fastening flange 18 of the carrier sleeve 16.

The stop sleeve 32 is pushed onto a proximal end section of the carrier sleeve 16 of the quick coupling 4, which forms an axial stop for the head section 42 together with a radial collar when the guide sleeve 6 is coupled. Distally spaced from the proximal end section of the carrier sleeve 16, said carrier sleeve comprises four circumferentially equally distributed, first, radial through-recesses 44, in which the four first balls 26 (first catching means) are received. The first, radial through-recesses 44 are conically tapered radially inward, so that it is ensured that the first balls 26 do not fall into the receiving space 40 of the carrier sleeve even when the guide sleeve 6 is removed and remain in the wall of the carrier sleeve 16.

The first balls 26 of the quick coupling 4 are provided to couple the guide sleeve 6 into the carrier sleeve 16. For this purpose, the guide sleeve 6 has a row of first coupling recesses 46 on its outer circumference that are adapted to the first balls 26. In the exemplary embodiment shown, this is realized by a plurality of spherical coupling recesses 46 on the outer circumference of the guide shaft 38, so that when the first balls 26 engage in the first coupling recesses 46, a rotational orientation of the guide sleeve 6 is also defined, which enables a rotational orientation of the instrument or device that can be arranged therein. Alternatively, only a first coupling recess 46 is provided, which is configured as a circumferential groove, so that a rotational orientation of the guide sleeve 6 in the carrier sleeve 16 cannot be defined.

To actuate the first balls 26, i.e. to engage the first balls 26 radially inward and to release the first balls 26 radially outward, the quick coupling 4 has the first, radially inner coupling sleeve 28, which is essentially cylindrical and which is slidably guided on the outside circumference of the carrier sleeve 16 in the axial direction, so that it can move over the first balls 26 in the axial direction with their different inner diameters. Accordingly, the first radially inner coupling sleeve 28 has at a proximal end portion a first circular cylindrical recess 48 with a first, larger inner diameter. In the distal direction, a first radial shoulder 50 is tapered radially inward. The first radial shoulder 50 tapers down to a second, smaller inner diameter of a second, distally formed, circular-cylindrical recess 52 of the first, radially inner coupling sleeve 28.

A movement of the first balls 26 through the first radially inner coupling sleeve 28 from its first, larger inner diameter to its second, smaller inner diameter thus leads to the engagement of the first balls 26 radially inwards into the first coupling recesses 46, and thus to the fixing of the guide sleeve. However, retracting the first, radially inner coupling sleeve 28—from the second, smaller inner diameter to the first, larger inner diameter-leads to the disengagement of the first balls 26 radially outward and to the release of the guide sleeve 6.

According to FIG. 8, the first radially inner coupling sleeve 28 is firmly connected to the actuating sleeve 14 via the connecting pins 22, so that a movement coupling of the two components is given. In this way, it is in particular possible to detect at the position of the actuating sleeve 14 whether the inserted guide sleeve 6 is engaged or whether it is disengaged.

According to FIG. 9, the first, radially inner coupling sleeve 28 has second, radial through-recesses 54—which lie outside the section guide according to FIG. 8, so that they are not visible there—in which the second balls 24 (second locking means) are received in a radially movable manner.

To actuate the second balls 24, i.e. to engage the second balls 24 radially inward and to release the second balls 24 radially outward, the quick coupling 4 has the second, radially outer coupling sleeve 30, which is essentially cylindrical and which is slidably guided on the outside circumference on the first, radially inner coupling sleeve 28 in the axial direction, so that it can move over the second balls 24 in the axial direction with their different inner diameters. Due to the coaxial and overlapping arrangement and guidance of the two coupling sleeves 28 and 30 results in a very space-saving design of the quick coupling. The second, radially outer coupling sleeve 30 has at a proximal end portion a first circular cylindrical recess 58 with a first, larger inner diameter. In the distal direction, a second radial shoulder 60 is tapered radially inward. The second radial shoulder 60 tapers down to a second, smaller inner diameter of a second, distally formed, approximately circular-cylindrical recess 62 of the second, radially outer coupling sleeve 30.

A movement of the second balls 24 through the second, radially outer coupling sleeve 30 from its (proximally arranged) first, larger inner diameter to its (distally arranged) second, smaller inner diameter thus leads to the engagement of the second balls 24 radially inward into second coupling recesses 64 of the carrier sleeve 16 arranged radially on the outer circumference (cf. FIG. 8), and thus to the fixing of the first, radially inner coupling sleeve 28 to the carrier sleeve 16. However, moving the second, radially outer coupling sleeve 30 back—from the second, smaller inner diameter to the first, larger inner diameter—leads to the disengagement of the second balls 24 radially outward and to the release of the first, radially inner coupling sleeve 28 from the carrier sleeve 16.

According to FIG. 8, the connecting pins 22 engage radially inward in the slot-shaped through-recess 68 of the carrier sleeve 16. They do not grasp the through-recess 68 in order not to get into coupling with the guide sleeve. The through-recess 68 limits the axial stroke of the first radially inner coupling sleeve 28 and, due to the aforementioned movement coupling, also the axial stroke of the actuating sleeve 14. In addition, they provide anti-twisting protection of the first, radially inner coupling sleeve 28 and the actuating sleeve 14 relative to the carrier sleeve 16.

With reference to FIG. 9, it can be seen that the guide sleeve 6 has so far only been inserted loosely into the receiving space 40, namely to the extent that its own weight rests on the cone-shaped actuating elements 34 of the quick coupling 4. In order to enable this contact between the guide sleeve 6 and the actuating elements 34, the actuating elements 34 reach through the slot-shaped through-recess 66 of the carrier sleeve 16 radially inward, that is, into the receiving space 40. In this way, the through-recess 66 limits the axial stroke of the actuating elements 34 and the axial stroke of the second, radially outer coupling sleeve 30 due to the above-mentioned movement coupling. In addition, they provide anti-twisting protection of the second, radially outer coupling sleeve 30 relative to the carrier sleeve 16.

A further anti-twisting device and thus axial guidance is realized for the second, radially outer coupling sleeve 30 on the first, radially inner coupling sleeve 28, which becomes clear with reference in particular to FIG. 7. Here, it can be seen that the second, radially outer coupling sleeve 30 is divided into two partially circumferential sleeve sections 70 in a region of its second, smaller inner diameter towards its distal, second end section. Accordingly, a flange 72 of the first radially inner coupling sleeve 28 is divided into partially circumferential flange sections 74. As indicated in FIG. 7, in the assembled state, the sleeve sections 70 of the second, radially outer coupling sleeve 30 are in engagement with the gaps between the flange sections 74 of the first, radially inner coupling sleeve 28 and thus form the anti-twisting device and axial guidance.

With reference to FIG. 8, for example, the radially outwardly arranged actuating sleeve 14 has a proximally tapered external actuating cone with a slightly concavely shaped outer surface. The outer jacket surface is provided with a circumferential knurling. The conical shape and the knurling enable a good manual actuation of the actuating sleeve 14, in particular in its intended manual actuation direction from proximal to distal, or from top to bottom according to the figures, or towards the flange 18 of the carrier sleeve, or from its second fixing position B to its first receiving position A (see in particular FIGS. 4 and 5).

The interior space of the actuating sleeve 14 is divided in the axial direction into a proximal and a distal, respectively cylindrical, interior space section, wherein the division is arranged approximately at the level of the connecting pins 22 or the flange 72. The upper interior section essentially accommodates the first balls 26, the first, radially inner coupling sleeve 28, the second balls 24, the second, radially outer coupling sleeve 30 and the second spring 36. The first spring 20 is substantially accommodated in the lower interior section. The lower interior section has a radial shoulder radially inward, on which the first spring 20 is axially supported on the actuating sleeve 14.

On the other hand, the first spring 20 is axially supported on the flange 18 of the carrier sleeve 16.

The following is a description of how to engage and secure the guide sleeve 6 and how to disengage and release the guide sleeve 6.

Looking at FIG. 9, the guide sleeve 6 has, at its distal end portion, circumferentially distributed guide grooves 76 extending in the insertion direction, which are delimited proximally by a respective actuating section 78, in particular a respective front end surface of the guide groove 76. When the guide sleeve 6 is inserted into the receiving space 40, some of the actuating sections 78 come into contact with the actuating elements 34, which is shown in particular in FIG. 9. In this context, it should be noted that more guide grooves 76 are provided as actuating elements 34 in the shown design example, so that not each of the actuating sections 78 comes into contact with an actuating element 34.

A distal geometry of the guide sleeve 6 is designed by means of chamfers and rounding such that an insertion aid is formed for the two actuating elements 34 in the guide grooves 76. Since the actuating elements 34, as already explained above, are secured against rotation against the carrier sleeve by means of the through-recesses 66, the guide grooves 76 of the guide sleeve 6 slide onto the rotationally fixedly disposed actuating elements 34, i.e. the guide sleeve 6 performs a rotation about its longitudinal axis during insertion by interaction of the bevels and rounding of its distal end section until the guide grooves 76 slide onto the actuating elements 34.

In the state shown in FIGS. 8 and 9—prior to pressing in the guide sleeve 6—the second balls 24 are still overrun by the smaller inner diameter of the second, radially outer coupling sleeve 30 and are therefore engaged. The first, radially inner coupling sleeve is thus fixed to the carrier sleeve 16 via the second balls 24 in the position shown in FIGS. 8 and 9. Therefore, the first balls 26 are not yet engaged and the guide sleeve is disengaged.

The guide sleeve 6 is now pressed in further so that the actuating elements 34 are moved distally, or downwards in the figures. Since the second, radially outer coupling sleeve 30 is firmly connected to the actuating elements 34 and is thus coupled in a motion-coupled manner, the second, radially outer coupling sleeve 30 is thereby carried distally, i.e. downwards in FIG. 9. It is entrained against the spring force of the second spring 36. This entrainment causes the second, radially outer coupling sleeve 30 to retract, so that the second balls 24 come into contact with the second radial shoulder 60 and are thus released radially outward from the second, radially outer coupling sleeve 30.

Subsequently, the first radially inner coupling sleeve 28 is no longer fixed to the carrier sleeve 29, i.e. released. Meanwhile, the spring force of the first spring 20 acts on the first, radially inner coupling sleeve 28 and preloads it in a proximal direction of movement.

If the first coupling recesses 46 now reach the first balls 26 by further pressing into the guide sleeve 6, they can engage radially inward. The pretensioning force of the first spring 20 now shifts the first radially inner coupling sleeve 28 proximally, so that the first balls are pushed over by the smaller inner diameter of the first radially inner coupling sleeve 28. The first balls 26 are thus engaged by the first, radially inner coupling sleeve 28 into the first coupling recesses 46 of the guide sleeve 6 under constant pressure, and the latter is thus securely fixed and orientated on the carrier sleeve 16.

In this state, the actuating sleeve 14 has its second fixing position B and the coupling mechanism of the quick coupling 4 has its second engaged position (cf. FIGS. 3 and 4).

Starting from this state, the guide sleeve 6 is now being disengaged.

None of the figures shows a sectional representation of this state, so that it is briefly summarized. Viewed from the outside, the quick coupling system 2 has this state in FIGS. 3 and 4. The following state is present in the interior of the quick-release system 2 (for example, with reference to FIG. 8): the guide sleeve 6 is pressed in until it stops. The actuating elements 34 are actuated distally, as is the second, radially outer coupling sleeve 30—due to the connection with the actuating elements 34. The second, radially outer coupling sleeve 30 is displaced proximally, so that the first balls 26 are passed over by the second, radially outer coupling sleeve 30 with their smaller inner diameter, and as a result the first balls 26 are engaged into the first coupling recesses 46 of the guide sleeve 6. The second balls 26 are not engaged. The first, radially inner coupling sleeve 28 is thus clamped into its position solely due to the spring force of the first spring 20.

Starting from this state, the actuating sleeve 14 is actuated distally or downwards according to the figures in order to release the guide sleeve 6 (cf. in particular the arrows in FIG. 3). As a result, the actuating sleeve 14 carries the first, radially inner coupling sleeve 28. The compressed, second spring 36 relaxes and the second, radially outer coupling sleeve 30 moves distally. As soon as the first balls 26 are released from the first, radially inner coupling sleeve 28, the second spring 36 acts and pushes the guide sleeve 6 proximally by means of the actuating elements 24 (cf. FIG. 5). The actuating sleeve 14, which is actuated distally to the stop, pulls the first radially inner coupling sleeve along until the second balls 24 again fix it to the carrier sleeve 16. Subsequently, the actuating sleeve 14 assumes its first receiving position A and the coupling mechanism its first engaged position.

FIGS. 12 to 17 each show, in a perspective full or partial view, exemplary embodiments of guide sleeves 6 of a medical quick coupling system 2 according to the disclosure.

Figure 12:
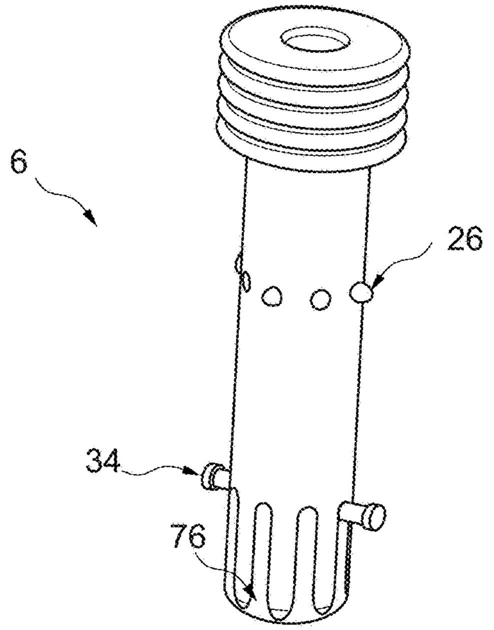
FIGS. 12 through 17 each show, in a perspective full or partial view, exemplary embodiments of guide sleeves of a medical quick coupling system according to the disclosure.

FIG. 12 shows a guide sleeve 6 with ten first coupling recesses (and first balls 26 accommodated therein) that is modified compared to the exemplary embodiment according to the preceding figures. For illustration purposes, the actuating elements 34 are visualized interacting with the guide grooves 76.

Figure 13:
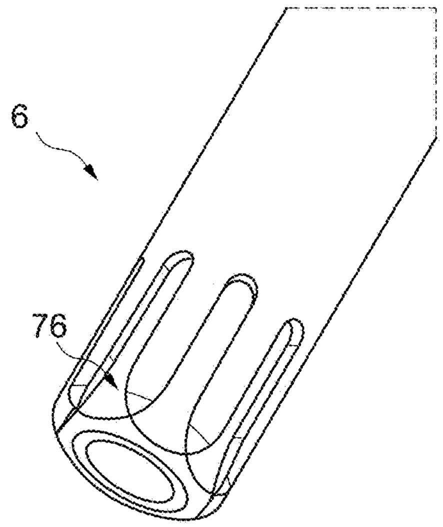

FIG. 13 shows the guide sleeve 6 according to FIG. 2 in a perspective partial view from below. This makes it clear that the guide grooves 76 end with chamfers and rounding in the distal end section of the guide sleeve 6, which facilitates the sliding of the guide grooves 76 onto the actuating elements 34 or the sliding of the actuating elements 34 into the guide grooves 76.

Figure 14:
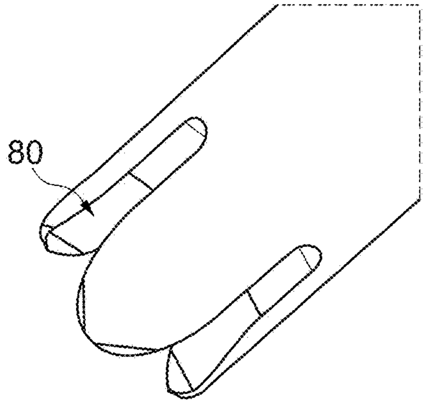
Figure 15:
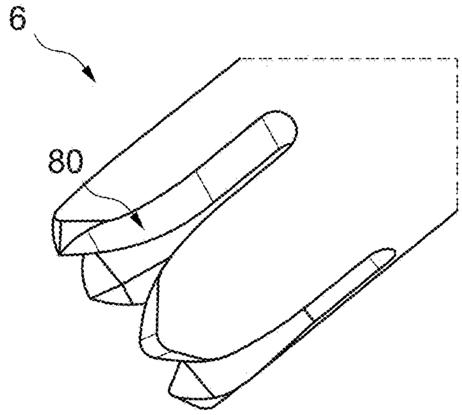

FIGS. 14 and 15 each show a variant of a guide sleeve 6, with guide recesses 80 instead of guide grooves. In FIG. 14, three guide recesses 80 are provided, and in FIG. 15, four. Here, too, the design of the 76 distal end section with chamfers and rounding proves to be advantageous.

Figure 16:
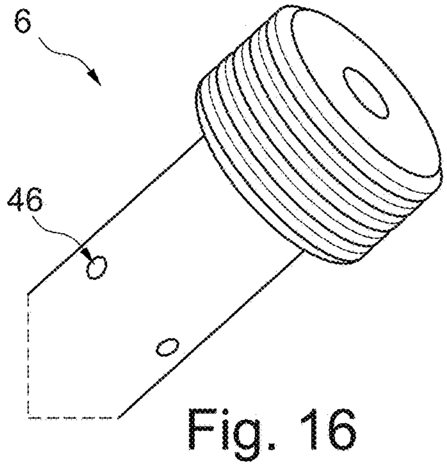

FIG. 16 shows the design of the guide sleeve 6 with several circumferentially distributed first coupling recesses 46, as already explained in the exemplary embodiment according to FIGS. 1 to 11, whereby in cooperation with the first balls 26 a rotational orientation of the guide sleeve 6 is enabled.

Figure 17:
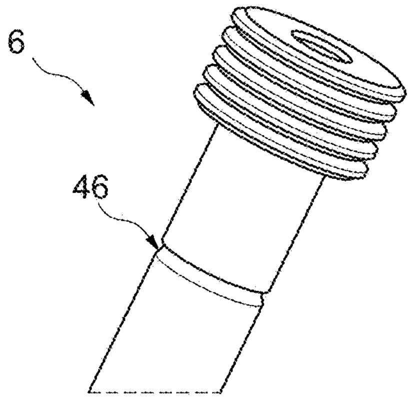

In contrast, FIG. 17 shows the design of the guide sleeve 6 with only one circumferential groove as the first coupling recess 46, which, in cooperation with the first balls 26, enables any rotational orientation of the guide sleeve 6.

LIST OF REFERENCE SIGNS

1 Medical quick coupling system
2 Guide sleeve
4 Quick coupling
6 Guide sleeve
8 Fastening adapter
10 End segment of robot
12 Screw gear
14 Actuating sleeve
16 Carrier sleeve
18 Carrier flange
20 First spring
22 Connection pin
24 Second ball
26 First ball
28 First, radially inner coupling sleeve
30 Second, radially outer coupling sleeve
32 Stop sleeve
34 Actuating element
36 Second spring
38 Guide shaft
40 Receiving space
42 Head section
44 First radial through-recess
46 First coupling recess
48 First round cylindrical recess
50 First radial shoulder
52 Round cylindrical recess
54 Second, radial through-recess
58 Round cylindrical recess
60 Second radial shoulder
62 Round cylindrical recess
64 Second coupling recess
66 Slotted through-hole recess
68 Slotted through-hole recess
70 Sleeve section
72 Flange
74 Flange section
76 Guide groove
78 Operating section
80 Guide recess
A First receiving position
B Second fixing position

The invention claimed is:

1. A medical quick coupling system for mounting a guide sleeve without tools, the medical quick coupling system comprising:

at least one guide sleeve having a guide axis in which a medical instrument or a medical device is receivable and alignable or orientable in a direction of the guide axis;

a quick coupling having a carrier sleeve arranged proximally in an insertion direction of the at least one guide sleeve and into which the at least one guide sleeve is receivable, and a radially outer actuating sleeve, which is movable relative to the carrier sleeve with a first receiving position and a second fixing position; and a coupling mechanism disposed between the actuating sleeve and the carrier sleeve, the coupling mechanism being adapted so that an insertion of the at least one guide sleeve into the quick coupling moves the coupling mechanism from a first disengaged position into a second engaged position, the coupling mechanism thereby moving the actuating sleeve from the receiving position into the fixing position, the coupling mechanism further being adapted so that an actuation of the actuating sleeve from the second fixing position against a pretension force into the first receiving position moves the coupling mechanism from the second engaged position into the first disengaged position, and the coupling mechanism comprises a first coupling sleeve and a second coupling sleeve, the first coupling sleeve and the second coupling sleeve being coaxially arranged and axially displaceable in an intermediate space between the carrier sleeve and the actuating sleeve, wherein the first coupling sleeve has a first sleeve section with a larger, first inner diameter and a second sleeve section with a smaller, second inner diameter, viewed in an axial direction, and wherein the first coupling sleeve cooperates with a first locking means in such a way that the first coupling sleeve engages the first locking means radially inwardly by moving over the first locking means from the larger, first inner diameter to the smaller, second inner diameter, which engages in the at least one guide sleeve in a form-fitting manner, so that the at least one guide sleeve is coupled to the carrier sleeve, wherein the first coupling sleeve interacts with the first locking means in such a way that the first coupling sleeve releases the first locking means radially outwards when moving back from the smaller, second inner diameter to the larger, first inner diameter, so that the at least one guide sleeve is uncoupled from the carrier sleeve.

2. The medical quick coupling system according to claim 1, wherein the coupling mechanism has at least one actuating element that protrudes radially into a receiving space of the carrier sleeve through a through-hole of the carrier sleeve, so that the actuating element is taken along by the at least one guide sleeve when inserted in an insertion direction.

3. The medical quick coupling system according to claim 2, wherein the at least one guide sleeve has at least one actuating section, which is provided and designed to engage with the at least one actuating element during insertion.

4. The medical quick coupling system according to claim 3, wherein the at least one actuating section is formed by a radially extending end face of a guide groove or guide recess extending into a distal end section in the insertion direction.

5. The medical quick coupling system according to claim 4, wherein a plurality of guide grooves or guide recesses are arranged with the end faces distributed circumferentially, and wherein an insertion section of the at least one guide sleeve is chamfered and/or rounded, into which the guide grooves or guide recesses run out in a chamfered or rounded manner, whereby an insertion aid of the at least one actuating element into the respective guide groove or guide recess and/or an aid for sliding the respective guide groove or guide recess onto the at least one actuating element is formed.

6. The medical quick coupling system according to claim 1, wherein the second coupling sleeve has, as seen in the axial direction, a first sleeve section with a larger, first inner diameter and a second sleeve section with a smaller, second inner diameter, and wherein the second coupling sleeve cooperates with a second, radially outer locking means in such a way that the second coupling sleeve moves over the second, radially outer locking means from the larger, first inner diameter to the smaller, second inner diameter, the second, radially outer locking means radially inward, which engages in the carrier sleeve in a form-fitting manner, so that the first coupling sleeve is coupled to the carrier sleeve, and wherein the second coupling sleeve is connected to the second, radially outer locking means of the coupling mechanism cooperates in such a way that the second coupling sleeve releases the second, radially inner locking means radially outwards again when moving back from the smaller, second inner diameter to the larger, first inner diameter so that the first coupling sleeve is uncoupled from the carrier sleeve.

7. The medical quick coupling system according to claim 1, wherein the first coupling sleeve is coupled to the actuating sleeve in a motion-coupled manner.

8. The medical quick coupling system according to claim 2, wherein the second coupling sleeve is motion-coupled to the at least one actuating element.

9. The medical quick coupling system according to claim 1, wherein the coupling mechanism has a first spring by which the actuating sleeve is prestressed in a direction of the second fixing position and the first coupling sleeve which is coupled in motion to the actuating sleeve is prestressed in a direction of movement of the first locking means from the larger, first inner diameter to the smaller, second inner diameter.

10. The medical quick coupling system according to claim 9, wherein the coupling mechanism has a second spring by which the second coupling sleeve is supported on the first coupling sleeve, and by which the second coupling sleeve is pre-stressed in the direction of passing over the second locking means from the larger, first inner diameter to the smaller, second inner diameter.

11. The medical quick coupling system according to claim 1, wherein:

the at least one guide sleeve comprises a first guide sleeve and a second guide sleeve, the first guide sleeve and the second guide sleeve having interfaces effective to the coupling mechanism that are identical or at least have a same effect, and the first guide sleeve and the second guide sleeve having different receptacles for receiving the medical instrument or the medical device.

* * * * *